United States Patent

Ebeling et al.

[11] Patent Number: 6,145,389
[45] Date of Patent: Nov. 14, 2000

[54] PEDOMETER EFFECTIVE FOR BOTH WALKING AND RUNNING

[76] Inventors: W. H. Carl Ebeling, 6212 39th Ave. NE., Seattle, Wash. 98115; Amara Ebeling, 4002 Burke Ave. N., Seattle, Wash. 98103

[21] Appl. No.: 08/970,174

[22] Filed: Nov. 13, 1997

Related U.S. Application Data

[60] Provisional application No. 60/030,743, Nov. 12, 1996.

[51] Int. Cl.$^7$ ........................................ A61B 5/00
[52] U.S. Cl. .............................. 73/865.4; 73/865.4
[58] Field of Search ................... 73/865.4; 364/565, 364/569, 566, 561

[56] References Cited

U.S. PATENT DOCUMENTS

| | | | |
|---|---|---|---|
| 3,580,083 | 5/1971 | Zipser | 73/865.4 |
| 4,371,945 | 2/1983 | Karr et al. | 364/561 |
| 4,578,769 | 3/1986 | Frederick | 364/565 |
| 4,855,942 | 8/1989 | Bianco | 364/561 |
| 5,485,402 | 1/1996 | Smith et al. | 364/566 |
| 5,574,669 | 11/1996 | Marshall | 364/569 |
| 5,724,265 | 3/1998 | Hutchings | 364/565 |

*Primary Examiner*—Benjamin R. Fuller
*Assistant Examiner*—Jewel V. Thompson

[57] ABSTRACT

A pedometer is disclosed that accurately calculates the length of the strides taken by a user when walking and running. The length of each stride is calculated using measurements of the acceleration of the wearer's foot during each stride. This acceleration is measured by an accelerometer attached either directly or indirectly to the wearer's foot. The calculation of the stride length is performed by a data processor which analyzes the accelerations of the foot as measured by the accelerometer. The acceleration values for each stride are identified, and these are used in conjunction with a set of coefficients to calculate the length of each stride. These coefficients are determined for each user by means of a calibration process during which the pedometer measures the characteristics of the wearer's stride for a variety of different walking and running speeds. Since the length of each stride is calculated independently, the user can change walking and running speeds and gaits without affecting the accuracy of the distance calculation.

12 Claims, 6 Drawing Sheets

PEDOMETER EFFECTIVE FOR BOTH WALKING AND RUNNING

CROSS-REFERENCES TO RELATED APPLICATIONS

This application claims the benefit of Provisional Patent Application Ser. No. 60/030,743 filed Nov. 12, 1996.

BACKGROUND

1. Field of Invention

This invention relates to pedometers, specifically to pedometers that measure the stride length of the wearer.

2. Description of Prior Art

Pedometers are devices for measuring the distance traveled by a person when walking and running. By using a device for measuring time in conjunction with the pedometer, the elapsed time taken to travel a distance can be measured and the average speed can be determined by dividing the distance traveled by the time taken to travel that distance.

In most of the prior art, pedometers do not determine the length of each individual step, but instead rely on a preset average stride length of the wearer. These pedometers count the number of steps and then compute the distance traveled by multiplying the step count by the preset average stride length. The accuracy of these pedometers depend on accurately counting the number of steps taken and accurately setting the preset stride length to the average stride length actually taken by the user. Since the stride length can vary greatly for different walking speeds and gaits, this method can be very inaccurate unless the person is careful to maintain the particular speed and gait that yields the preset average stride length. Running gaits vary even more widely in stride length than walking gaits and thus this method cannot accurately compute the distance traveled by runner.

Pedometers count the number of steps taken by the wearer using a variety of methods. Typical pedometers sense the up and down motion of the wearer caused by each stride by means of a weighted pendulum. The inertia of the pendulum causes it to move with relation to the pedometer. In mechanical pendulums, this motion is typically sensed using a ratchet mechanism, which advances a counter with each swing of the pendulum. (See U.S. Pat. No. 4,560,861 to Kato, et. al., Dec. 24, 1985.) Electrically instrumented pendulums typically use a switch contact which is closed by each swing of the pendulum. (See U.S. Pat. No. 5,117,444 to Sutton, et. al., May 26, 1992.) In either case, the pedometer must be adjusted according to the stride characteristics of the wearer. Some pedometers have a switch that can be set to "walk" or "run" while others allow a range of adjustments. A drawback to pedometers that rely on pendulums is this requirement that they be adjusted to the user's gait. This means that the wearer must maintain approximately the same gait or the pedometer will not count the steps taken by the user accurately.

Some pedometers count steps more directly by means of a sensor or sensors embedded in the shoe that are connected directly to a counter. This can be done mechanically where each step depresses a mechanism that causes a mechanical counter to increment. More frequently electrical means are used whereby an electrical switch is closed by each step, creating an electrical signal that causes an electronic counter to increment. (See U.S. Pat. No. 5,640,786 to Buyayez, Jun. 24, 1997.) This method counts the number of steps more accurately than pedometers that rely on pendulums. In particular, these pedometers allow the user to change gaits while walking and running. However, the accuracy of these pedometers is still limited to the accuracy of the preset stride length.

Some recent pedometers do not rely on a preset stride length, but use the rate at which steps are taken to estimate the length of each stride. (See U.S. Pat. No. 5,583,776 to Levi, et. al., Dec. 10, 1996.) The stride length is correlated to some extent to the step rate, but this correlation does not hold for different gaits and is not generally accurate for running speeds greater than 7 or 8 m.p.h. U.S. Pat. No. 5,583,776 further discloses a pedometer that incorporates an accelerometer, which is used as a more accurate alternative to the pendulum mechanism of ordinary pedometers. This patent discloses two methods for counting the number of steps taken. One method detects peaks in the acceleration data measured by the accelerometer which correspond to individual steps taken. A second method uses signal processing algorithms to extract the fundamental step frequency from the accelerometer data. The number of steps taken is then calculated by multiplying the elapsed time by the step frequency. The step frequency is also used to estimate the average stride length, relying on the correlation between step frequency and stride length. In this regard, U.S. Pat. No. 5,583,776 is similar to other prior art because it counts the users steps and estimates the stride length from the rate at which steps are taken. In particular, it does not measure the acceleration of the foot itself, and provides no advantage over other prior methods for counting steps or estimating stride length.

U.S. Pat. No. 4,371,945 to Karr, et. al., Feb. 1, 1983 discloses a device that directly measures the stride length by means of an ultrasonic distance measuring device that measures the distance between the wearer's feet when taking a step. This requires an ultrasonic transmitter strapped to one leg and an ultrasonic receiver strapped to the other leg, each connected to a processor that performs the distance calculation. This device is both cumbersome for the user to wear and more expensive than ordinary pedometers because of the ultrasonic devices required. U.S. Pat. No. 4,703,445 to Dassler, Oct. 27, 1987 discloses a device that operates in a similar manner using ultrasonic transmitters in both shoes.

U.S. Pat. No. 4,736,312 to Dassler, et. al., Apr. 5, 1988 discloses a device that measures the stride length of a runner by measuring the elapsed time between the time when one foot lifts off the ground and the time when the other foot hits the ground during a stride. This provides a more accurate estimation of stride length than possible using the step frequency alone. However, the shoes on both feet are equipped with sensors, and the data from both must be communicated to a central processor which performs the distance calculation. Thus this arrangement is not a self-contained unit that can be worn by the user. Since it is comprised of three different components, it is also more expensive to make than a single unit.

U.S. Pat. No. 5,485,402 to Smith, et. al., Jan. 16, 1996 discloses a gait activity monitor that records the number of steps taken by the wearer. This monitor incorporates an accelerometer attached to the ankle of the wearer, which measure the acceleration of ankle. A data processor processes this acceleration data, counting and recording the number of steps taken during each measurement time interval. This monitor, however, does not calculate any distance traveled. Moreover, it is not a self-contained unit that the user can portably wear.

OBJECTS AND ADVANTAGES

Accordingly, several objects and advantages of the present invention are:

(a) to provide a pedometer which accurately measures the distance traveled over a wide range of walking and running speeds;
(b) to provide a pedometer which accurately measures the distance traveled even if the wearer changes speeds and gaits during use;
(c) to provide a pedometer which is small and light enough to be worn on the shoe without encumbering the wearer;
(d) to provide a pedometer which is small and light enough to be manufactured as part of a shoe; and
(e) to provide a pedometer which can be easily and accurately calibrated for the individual user.

Further objects and advantages of our invention will become apparent from a consideration of the drawings and ensuing description.

DRAWING FIGURES

Figure 1:
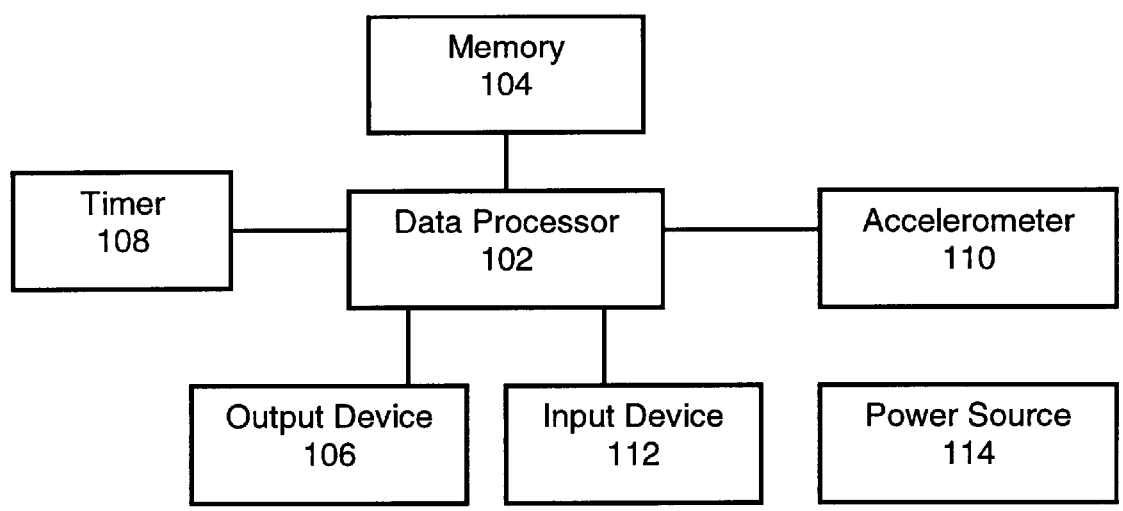
FIG. 1 is a block diagram of the components contained within the pedometer.

| Reference Numerals in Drawings | |
|---|---|
| 102 data processor | 104 memory |
| 106 output device | 108 timer |
| 110 accelerometer | 112 input device |
| 114 power source | |
| 402 quiescent region | 403 beginning of walking stride |
| 404 walking lift phase | 406 walking coast phase |
| 408 walking kick phase | 410 end of walking stride |
| 502 running impact region | 503 beginning of running stride |
| 504 running lift phase | 506 running coast phase |
| 508 running kick phase | 520 end of running stride/first acceleration decrease in running impact region |
| 521 acceleration increase in running impact region | 522 second acceleration decrease in running impact region |
| 602 accelerometer data stream | 604 data conditioning procedure |
| 606 acceleration data array | 608 stride analysis procedure |
| 610 stride profile data | 612 stride length calculation procedure |
| 614 stride length data | |

SUMMARY

The present invention is a device that measures the stride length of a person when walking or running. The device comprises a data processor coupled to an accelerometer attached to the user's foot. This device determines the length of each stride from the acceleration data measured by an accelerometer. This device can thus accurately calculate the distance traveled by the user, regardless of walking or running speed or gait.

DESCRIPTION

The present invention is a pedometer that operates by calculating the distance traveled by a person's foot when that person is walking or running. The length of each stride is calculated accurately from data provided by an accelerometer that measures the acceleration of the wearer's foot. The total distance traveled is computed as the sum of the individual stride lengths. Since the length of each stride is calculated independently, this pedometer calculates the distance traveled accurately even if the person changes speed and gait while walking or running. It is necessary to measure the stride length for only one foot, since both feet travel the same distance.

Our invention comprises an accelerometer (110) and a data processor (102) connected together as depicted in FIG. 1. The data processor is further connected to an output device (106) which is used to display information to the user. In the preferred embodiment, this output device is a liquid crystal display (LCD) that is placed on the instep of the shoe or on the toe of the shoe so that it is easily visible to the user. The walker can read the information while walking whenever the foot with the display is on the ground and therefore stationary with respect to the eye.

Also connected to the data processor is a memory (104) comprising both volatile and non-volatile memory. The non-volatile memory is used to store the program instructions and data. The non-volatile memory is further used to store coefficient data that specializes the distance calculation formula for a particular user. This coefficient data is written to the memory during a calibration process and thus at least part of the non-volatile memory must be writeable. This can be accomplished using EEPROM memory as is well-known in the art. The volatile memory is used by the data processor as temporary storage while performing the distance calculation.

The data processor is further connected to a timer (108) which provides a means of measuring the elapsed time. This elapsed time is used to calculate the speed of travel. The timer can optionally be used in addition to provide a clock function.

The data processor may be further connected to an input device (112) which provide the user the means of operating the pedometer. Such operations may include turning the pedometer on and off; enabling the display of different information such as the total distance traveled, the speed of travel or the elapsed time; and restarting or pausing the distance measurement. In the preferred embodiment, the user additionally operates the pedometer using a simple communication method based on tapping the toe on the ground. For example, tapping the toe twice in rapid succession could be used to reset the distance measurement and time. A single tap could be used to pause the time and distance measurement and another tap to resume measurement. This tapping is performed by raising the foot so that the sole is perpendicular to the ground and tapping the toe on the ground. This produces foot accelerations that are distinctly different from that produced by walking or running, and these are easily recognized by the data processor.

A power source (114) is also provided to provide electrical power to the pedometer. In the preferred embodiment, a lithium battery is used for the power source.

Microprocessors are currently available that combine a data processor, volatile and non-volatile memory, including EEPROM memory, and a timer in a single integrated chip. An example is the Atmel AT89S8252 8-bit microcontroller. The remaining components are sufficiently small that the entire pedometer can be put into a package the size of a small wristwatch. The pedometer is thus small enough and light enough to be worn on the shoe or in the shoe without impeding the wearer. It will be appreciated that the pedometer as described need not be assembled in a single package, but could comprise discrete parts connected together.

The accelerometer (110) is attached to the foot of the wearer and measures the acceleration of the wearer's foot in the direction of travel. The accelerometer can be attached to the foot by a number of means, including by means of a band to attach it to the ankle, or by attaching it to the shoe, or by embedding it directly in the shoe itself. The accelerometer is attached to the foot so that the axis of acceleration measurement is aligned more or less with the direction of travel. This alignment does not have to be precise and can be as much as 30 degrees, or more, out of alignment with respect to the direction of travel. The accelerometer measures the rate of change in velocity of the foot along the axis of measurement. If this axis is not aligned with the direction of travel, the acceleration measured is a combination of the acceleration in the forward and lateral directions. Since there is little or no lateral movement of the foot while walking and running, the value measured is $A' = A \cos \theta$, where A is the acceleration in the direction of travel and $\theta$ is angle between the axis of acceleration measurement and the direction of travel. If the accelerometer is securely fastened, then this angle $\theta$ is constant, and the measured value A' is the actual acceleration scaled by a constant factor. If the device is worn the same way each time it is used, the values from one session to the next will differ only slightly for the same motions of the foot. If the accelerometer is mounted so that the axis is nearly aligned with the direction of travel, then differences in mounting will cause little difference in the measured value since the cosine of small angles is very nearly 1.0.

Figure 2:
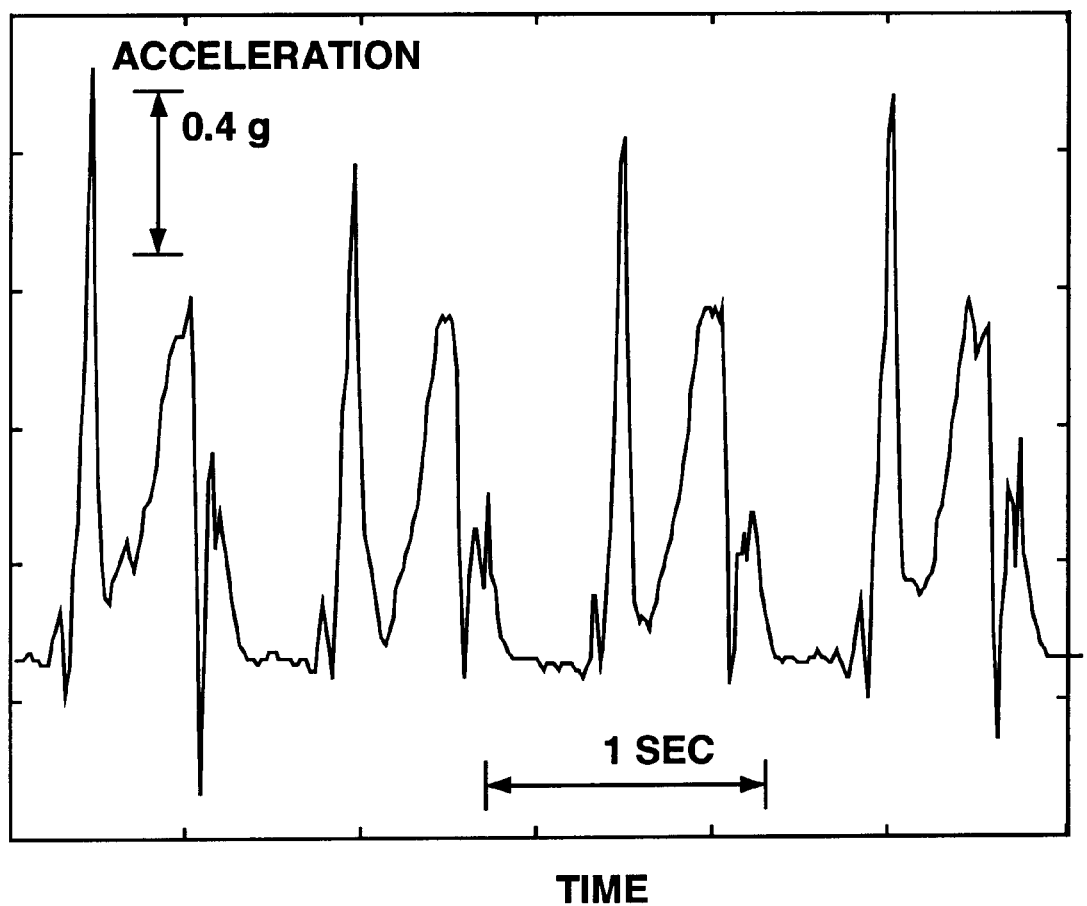
FIG. 2 is a graph of the forward acceleration of the foot for several representative walking strides.
Figure 3:
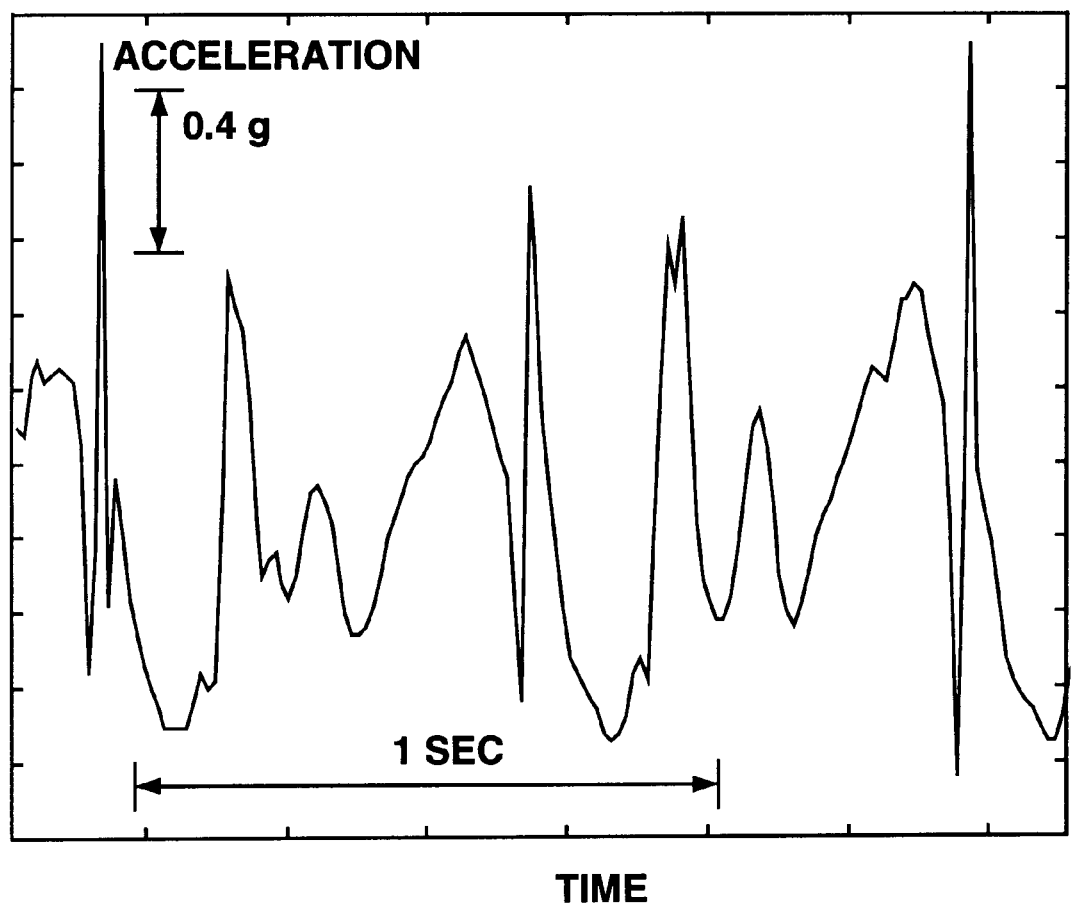
FIG. 3 is a graph of the forward acceleration of the foot for several representative running strides.

In the currently preferred embodiment, the accelerometer (110) is a silicon accelerometer such as the Analog Devices ADXL05. The accelerometer used in this invention should have a range of measurement of about −4 g/+4 g and be capable of measuring instantaneous acceleration at a rate of up to 250 samples/second with an accuracy of about 0.03 g. In the currently preferred embodiment, the Analog Devices ADXL05 outputs the measured acceleration as an analog value that is directly proportional to the measured acceleration. This analog value is first converted to an 8-bit digital value using an analog-to-digital (A-D) converter before being used by the data processor. Many microprocessors have analog-to-digital (A-D) converters integrated on the same integrated circuit, obviating the need for a separate A-D converter. FIG. 2 shows an example of the forward acceleration of the foot of a person walking as measured by the Analog Devices ADXL05 accelerometer attached to the shoe. FIG. 3 shows an example of the forward acceleration of the foot of a person running.

The data processor (102) is connected to the accelerometer (110) to receive the acceleration data measured by the accelerometer. In the currently preferred embodiment, the data processor and accelerometer are combined into a single unit attached to the foot. This unit is attached to the foot by some means, for example, by means of a strap or elastic band attached to the ankle, by means of attachment to the shoe or by means of embedding directly in the shoe itself. The means of attachment is not important insofar as the accelerometer is positioned in such a way that it measures the acceleration of the foot in the direction of travel, as described previously. The preferred means of attachment is to attach the device to, or embed the device in, a walking shoe or running shoe in such a way that it can be removed and used for different shoes. Since silicon accelerometers are fabricated using the same integrated circuit technology as microprocessor s, the accelerometer can be integrated onto the same integrated circuit as the microprocessor.

Analysis of foot acceleration data

The data processor receives data from the accelerometer, which measures the instantaneous acceleration of the foot in the direction of travel. This acceleration is sampled many times per second. This data is processed and analyzed in order to calculate the distance traveled by the foot by each stride. It is necessary to calculate the distance traveled by only one foot since both feet travel the same distance.

Figure 4:
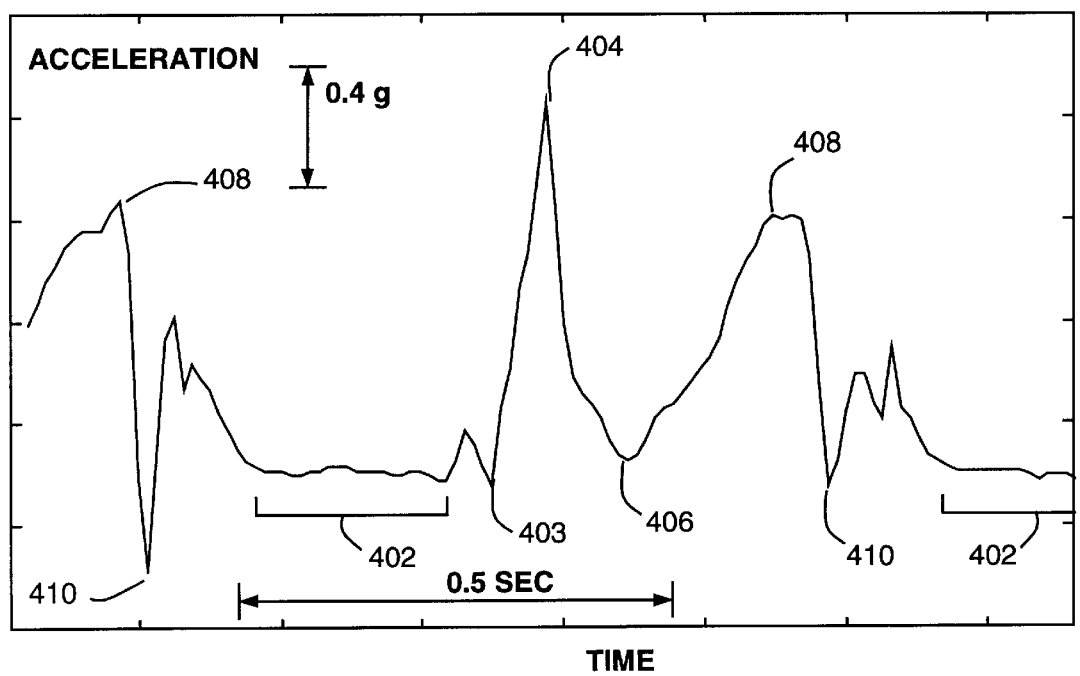
FIG. 4 is a graph of the forward acceleration of the foot for one representative walking stride.
Figure 5:
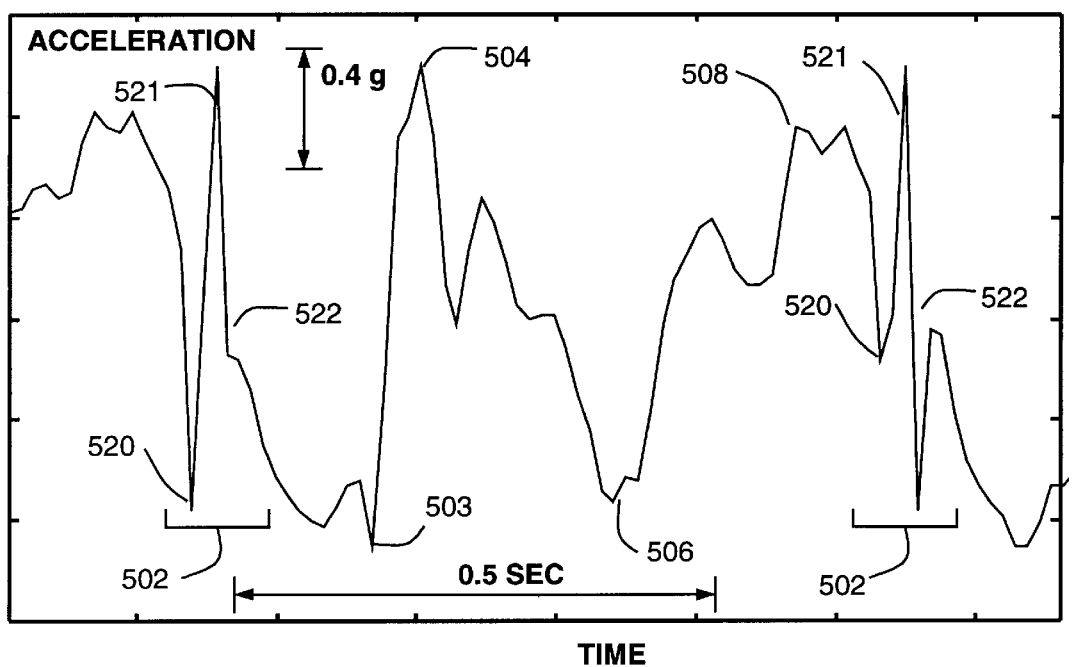
FIG. 5 is a graph of the forward acceleration of the foot for one representative running stride.

We call the acceleration data collected during a single stride the stride profile. FIG. 4 shows the stride profile for a representative walking stride. The stride profile is similar for different people and for different walking speeds. FIG. 5 shows the stride profile for a representative running stride. The stride profile for running is somewhat different from the walking profile, but it too is similar for different people and for different running speeds. The acceleration data is first analyzed to identify the beginning and end of each stride. The acceleration data is then further analyzed to identify specific events that occur during the course of a stride. This analysis produces a set of values that characterize each stride. This set of values is used to directly calculate the length of each stride.

Figure 6:
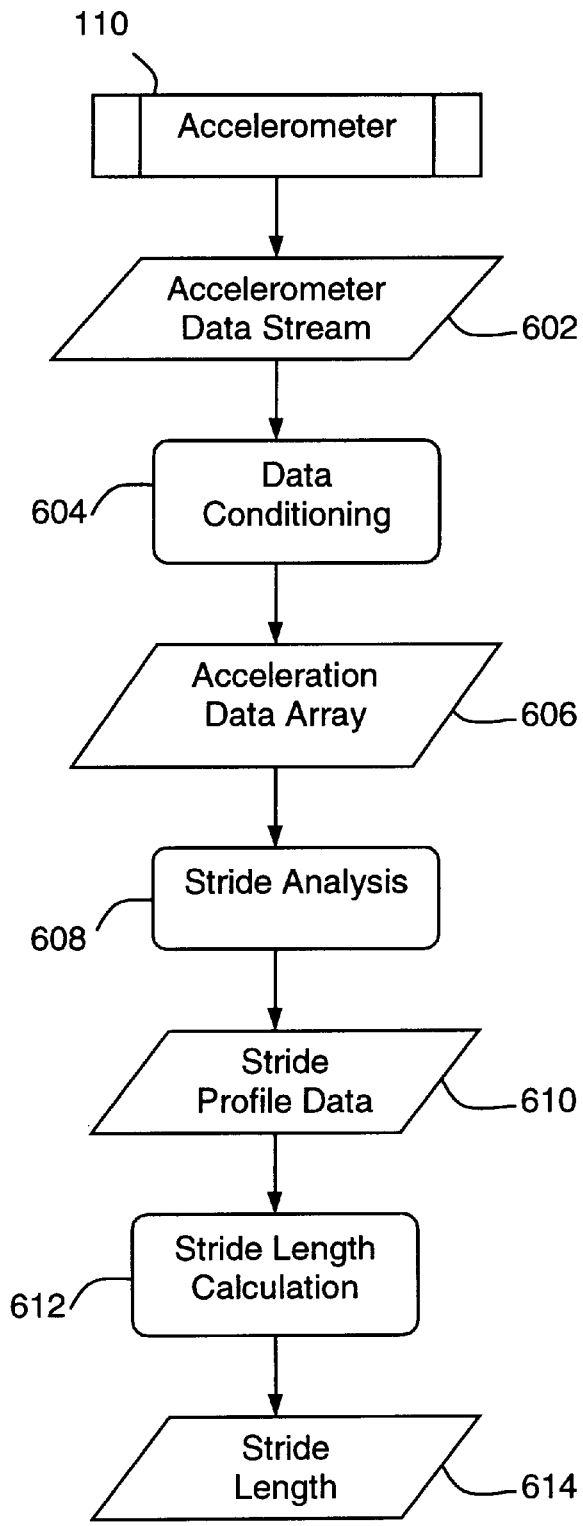
FIG. 6 is a flowchart showing the data flow by which the acceleration data measured by the accelerometer is processed to determine the stride length.

FIG. 6 gives the overall data flow of the process that analyzes the acceleration data measured by the accelerometer (110) and calculates the length (614) of each stride. The data processor samples the data provided by the accelerometer at a rate sufficient to produce a well-defined stride profile. In the preferred embodiment, a sample rate of 150 Hz. is used. This sampling process produces a stream of acceleration data values (602).

Before these data values (602) are stored and analyzed, the data is conditioned (604) by removing the acceleration bias caused by gravity and the way the accelerometer is mounted on the shoe. This bias is removed by subtracting from each data sample the mean value of the acceleration data sampled during the time period immediately preceding the data sample. In the preferred embodiment, the length of this time period is five seconds. The data measured by the accelerometer may be further conditioned by filtering to remove noise introduced by the accelerometer or by the way it is attached to the foot.

After conditioning, the acceleration data samples are stored sequentially in the processor memory in a data structure called the acceleration data array (606). The acceleration data array contains the data that has been sampled, but not yet processed. As data is sampled, it is added to the end of this data array, and when data is finished being processed, it is removed from the beginning of the array. Thus only data not yet processed remains in the acceleration data array. Those skilled in the art will recognize that a data structure called a software FIFO can be used to implement the acceleration data array (606).

The data in the acceleration data array is processed by a process (608) that examines the data sequentially starting at the beginning, examining it first for the features that distinguish a walking stride from a running stride. The walking stride profile is distinguished by a region of relatively constant acceleration (402) which occurs when the foot is on the ground between steps. We call this region the "quiescent" phase of the stride. Running step profiles are distinguished by a region of very high change in acceleration (502) which is caused by the foot hitting the ground at the end of a step. This region starts with a large but brief decrease in acceleration (520), followed by a large but brief increase in acceleration (521), followed by a large but brief decrease in acceleration (522). We call this region the "running impact" phase of the stride. Walking strides can be thus distinguished from running strides.

The stride analysis process (608) examines the data starting at the beginning of the acceleration data array for the first instance of either a quiescent region or a running impact region. If a quiescent region is found, then the input data is analyzed under the assumption that a walking step has taken place. If a running impact region is found, the data is analyzed under the assumption that a running step has taken place.

Walking Stride Profile Analysis

FIG. 4 shows the acceleration data profile for a representative walking stride. This stride begins with the foot on the ground during the quiescent phase (402). The quiescent phase ends when the foot is lifted from the ground (403). This lifting of the foot is marked by a large forward acceleration of the foot whose maximum marks the "lift" phase of the stride (404). The lift phase is followed by a decreased acceleration of the foot, called the "coast" phase (406) during which the foot experiences much less forward acceleration as it swings forward. The coast phase is followed by the "kick" phase (408), during which the foot again experiences a large forward acceleration prior to being placed on the ground. The forward acceleration of the foot decreases rapidly as the foot is placed on the ground (410).

The phases of the walking stride are further defines as follows. The quiescent phase (402) is defined as an interval of at least 0.25 seconds during which the acceleration of the foot changes by no more than 0.2 g, indicating that the foot is stationary.

The lift phase is defined as the first peak (404) in the acceleration data after the quiescent phase. This peak must have an acceleration value at least 0.4 g greater than the average acceleration value during the quiescent phase, and the peak must be followed by a decrease in acceleration of at least 0.4 g. A procedure for finding the peak is to examine the data in sequence beginning with the quiescent phase, maintaining the maximum value found so far. If data is found which is less than this maximum value by 0.4 g, and the current maximum value is sufficiently large, then the procedure terminates and the maximum value is called the lift value and the time at which this maximum value occurs relative to the beginning of the stride (403) is called the "time of the lift value". The beginning of the stride (403) is further defined as the time from which the acceleration values increase monotonically in value until the lift value, subject to the constraint that the acceleration value at the beginning of the stride (403) must be no more than 0.1 g greater than the average acceleration value in the quiescent region (402).

The coast phase (406) is defined as the first trough in acceleration data after the lift phase (404). This trough must have an acceleration value less than 0.4 g less than the lift value, and must be followed by an increase in acceleration of at least 0.4 g. A procedure for finding the coast trough is to examine the data in sequence beginning at the lift phase, maintaining the minimum value found so far. If data is found which is greater than this minimum value by 0.4 g, and the current minimum value is sufficiently small, then the minimum value is called the coast value and the time at which this minimum value occurs relative to the beginning of the stride (403) is called the "time of the coast value".

The kick phase (408) is defined as the first peak in the acceleration data after the coast phase. This peak must have an acceleration value at least 0.4 g greater than the coast value, and the peak must be followed by a decrease in acceleration of at least 0.4 g. A procedure for finding the kick peak is to examine the data in sequence beginning at the coast phase, maintaining the maximum value found so far. If data is found which is less than this maximum value by 0.4 g, and the maximum value is sufficiently large, then the maximum value is defined as the kick value and the time at which this maximum value occurs relative to the beginning of the stride (403) is called the "time of the kick value".

The first trough after the kick phase marks the end of the stride (410). This trough must have an acceleration value at least 0.4 g less than the kick value and must be followed by an increase in acceleration of at least 0.1 g. A procedure for finding the end of stride trough is to examine the data in sequence beginning with the kick peak, maintaining the minimum value found so far. If data is found which is greater than this minimum value by 0.1 g, and the minimum value is sufficiently small, then the time at which this minimum value occurs relative to the beginning of the stride (403) is called the time of the end of stride.

This analysis of the walking stride results in several values that characterize the walking stride precisely. These include:

1) The duration of the stride, defined as the elapsed time between the start of the stride (403) and the end of the stride (410).
2) The lift acceleration value.
3) The time of the lift value.
4) The coast acceleration value.
5) The time of the coast value.
6) The kick acceleration value.
7) The time of the kick value.
8) The sum of the acceleration values from the start of the stride to the time of coast. This represents the area under the curve in FIG. 4 from (403) to (406).
9) The sum of the acceleration values from the time of coast to the end of the stride. This represents the area under the curve in FIG. 4 from (406) to (410).

This set of nine data values resulting from the stride analysis process (608) forms a data vector called the stride profile data (610). This stride profile data is used by the stride length calculation (612) to calculate the stride length (614). It will be appreciated that this set of nine data values are those used in the currently preferred embodiment, but that other data derived from the stride analysis could be used, including a subset of these values.

Running Stride Profile Analysis

FIG. 5 shows the acceleration data profile for a representative running stride. The quiescent phase as defined for the walking stride does not appear in the running stride profile because the foot is on the ground for a shorter period and maintains movement even while the foot is in contact with the ground. The distinguishing feature of the running stride is the running impact region (502), which occurs when the foot hits the ground at the end of a stride. The running impact region is defined by three large changes in acceleration: First, there is a decrease in acceleration (520) of at least 0.6 g., followed by an increase in acceleration (521) of at least 0.6 g., followed by a decrease in acceleration of 0.8 g. (522). These three changes in acceleration must occur within 0.2 seconds.

The remainder of the running profile is similar to the walking profile. There is a lift phase (504), followed by the coast phase (506), followed by the kick phase (508), followed finally by the running impact region (502) which marks the end of the running stride.

The phases of the running stride are further defined as follows. The lift phase (504) is defined as the first peak in the acceleration data that occurs at least 0.1 seconds after the end of the impact region. This maximum acceleration value must be the result of an increase of at least 0.8 g in less than 0.2 seconds. The peak must then be followed by a decrease in acceleration of at least 0.8 g. A procedure for finding the lift peak is to examine the data in sequence beginning with data 0.1 seconds after the end of the impact region, maintaining the maximum value found so far. If data is found which is less than current maximum value by 0.8 g, and the maximum value is a result of an increase of at least 0.8 g in less than 0.2 seconds, then the procedure terminates and the maximum value found is called the lift value and the time at which this maximum value occurs relative to the beginning of the stride (503) is called the "time of the lift value". The beginning of the stride (503) is further defied as the time from which the acceleration values increase monotonically in value until the lift value, subject to the constraint that the acceleration value at the beginning of the stride must be less than 0.8 g less than lift value.

The coast phase (506) is defined as the first trough in acceleration data after the lift phase (504). This trough must have an acceleration value less than 0.8 g less than the lift value, and must be followed by an increase in acceleration of at least 0.6 g. A procedure for finding the coast trough is to examine the data in sequence beginning with the lift peak, maintaining the minimum value found so far. If data is found which is greater than this minimum value by 0.6 g, and the minimum value is sufficiently small, then the minimum value is defined as the coast value and the time at which this minimum value occurs relative to the beginning of the stride (503) is called the "time of the coast value".

The kick phase (508) is defined as the first peak in the acceleration data after the coast phase. This peak must have an acceleration value at least 0.6 g greater than the coast acceleration value, and the peak must be followed by a decrease in acceleration of at least 0.4 g. A procedure for finding the peak is to examine the data in sequence beginning with the coast phase, maintaining the maximum value found so far. If data is found which is less than this maximum value by 0.4 g, and the maximum value is sufficiently large, then the maximum value is defined as the kick value and the time at which this maximum value occurs relative to the beginning of the stride (503) is called the "time of the kick value".

The end of the stride is defined as the first trough in the acceleration data in the running impact region. That is, the minimum acceleration value that results from the first decrease in acceleration (520) marks the end of the stride and the time at which this minimum value occurs relative to the beginning of the stride (503) is called the time of the end of stride.

This analysis of the stride results in several values that characterize the running stride precisely. These include:
1) The duration of the stride, defined as the elapsed time between the start of the stride (503) and the end of the stride (520).
2) The lift acceleration value.
3) The time of the lift value.
4) The coast acceleration value.
5) The time of the coast value.
6) The kick acceleration value.
7) The time of the kick value.
8) The sum of the acceleration values from the start of the stride to the time of coast. This represents the area under the curve in FIG. 5 from (503) to (506).
9) The sum of the acceleration values from the time of coast to the end of the stride. This represents the area under the curve in FIG. 5 from (506) to (520).

This set of nine data values resulting from the stride analysis process (608) forms a data vector called the stride profile data (610). This stride profile data is used by the stride length calculation (612) to calculate the stride length (614). It will be appreciated that this set of nine data values are those used in the currently preferred embodiment, but that other data derived from the stride analysis could be used, including a subset of these values.

After the stride profile data (610) for a stride has been calculated, the acceleration data in the acceleration data array (604) up to the end of that stride is deleted. The stride analysis process (608) begins again at the beginning of the acceleration data array, examining the data for the next stride. Processing speeds of current data processors is sufficiently high that the stride analysis can be done much faster than the data is collected. Thus the stride analysis process may at times have to wait for acceleration data samples before continuing.

It will be appreciated that the acceleration and time values given here in the description of the process for analyzing strides are those used in the preferred embodiment, but that other, similar values, may be used.

Stride Length Calculation

The length of both the walking stride and the running stride is computed directly from the profile data vector produced by the stride analysis. The length of the stride is computed directly by the following formula:

$$\text{stride length} = a0 + (a1 \cdot d1) + (a2 \cdot d2) + (a3 \cdot d3) + (a4 \cdot d4) + (a5 \cdot d5) + (a6 \cdot d6) + (a7 \cdot d7) + (a8 \cdot d8) + (a9 \cdot d9)$$

where the values d1 through d9 are the nine values in the stride profile data vector already described, and the values a0 through a9 are constant walking stride length coefficients stored in memory. This stride length formula is used for both walking strides and running strides but two different set of coefficients are used, one set for walking strides and a second set for running strides. The stride analysis phase distinguishes between walking and running strides and this information is used to determine which set of coefficients is used to calculate the stride length. The stride length coefficients are defined for each individual user to provide an accurate stride length calculation for that user.

Calibration

The stride length coefficients are derived by means of a calibration process. During each session of the calibration process, the user walks a predetermined distance at a constant speed and gait. Several sessions are used to collect calibration data for a variety of walking speeds and gaits. During each session, the stride analysis process (608) computes the stride profile data vector for each stride. This set of stride profile data vectors is stored in memory for subsequent analysis along with the length of the stride. This stride length is the average stride length for the calibration session and is calculated by dividing the predetermined distance walked by the number of steps taken. This calibration process is repeated as many times as desired for different walking speeds. The result is a set of walking profile data vectors along with the corresponding stride lengths stored in the data processor memory. After this data has been collected, the walking stride length coefficients are calculated by performing a multiple linear regression using the data. Multiple linear regression is a well-known technique, described for example in Chapter 11 of the textbook "Probability and Statistics for Scientists and Engineers", 5th edition, by Ronald E. Walpole and Raymond H. Myers (Prentice-Hall: 1993). The walking stride coefficients calculated by the calibration process are stored in the non-volatile memory of the data processor and used subsequently by the stride length calculation (612) for walking strides.

This calibration process is also performed for running strides and the same procedure, as described in the previous paragraph, is used to calculate a set of running stride coefficients, which are also stored in non-volatile memory. The calibration sessions for walking and running can be intermixed. However, the stride profile data vectors are stored and processed independently for walking and running and the walking and running stride coefficients are calculated as if the calibration data were collected independently.

The walking and running stride length coefficients can be derived directly from the physical characteristics of the person using the pedometer. These coefficients are similar for people with similar physical characteristics. By calibrating the pedometer for people with a wide range of physical characteristics, tables of coefficient data can be determined. The coefficients for a particular person can then be set to the coefficients of someone who is physically similar. This procedure avoids the calibration process at some possible loss of accuracy.

Transients

While the user is continuously walking or running, the stride analysis is straightforward, even if the user changes speeds. However, when the user starts or stops walking or running or when the user changes from walking to running or running to walking to running, there are transients in the acceleration data that make it deviate from the normal walking or running profile. The startup and stopping cases typically result in a normal profile, although the first and last step may be classified as walking even if the runner is running. The small error that may occur is insignificant over an entire walking or running session. However, when changing between walking and running modes, the step analysis phase may not find either a quiescent phase or a running impact phase. In this case, the process may not be able to process a stride, or perhaps even several strides, even though it is apparent that the user is walking or running because the accelerometer data is not in the normal quiescent range that occurs when the user is standing still. The pedometer can fill in the distance of the missing strides by averaging the stride lengths for strides occurring before and after the missing strides. If only a few strides are missed, then the number of strides missed can be estimated accurately by dividing the time period during which no stride was detected by the average stride rate before the missing strides. This method is also useful whenever the acceleration data departs from the expected values for walking and running strides.

Conclusion, Ramifications and Scope

Accordingly, the reader will see that the pedometer of this invention can accurately measure the stride of a user while walking or running, and moreover this measurement is accurate over a wide range of different speeds and gaits. Furthermore, the pedometer can be calibrated for a particular user, either by entering data based on the person's physical characteristics, or by using a calibration method whereby the pedometer collects acceleration data for different walking and running speeds and gaits. The pedometer is also small and light and thus convenient and inconspicuous for the user to wear.

Although the description above contains many specificities, these should not be construed as limiting the scope of the invention but as merely providing illustrations of some of the presently preferred embodiments of this invention. For example, the usefulness of the pedometer described herein may extended in a number of ways. At times runners and joggers must stop running when their path is impeded, for example, by an intersection. The pedometer can optionally have a mode whereby the measurement of time is suspended while the user is stopped so that the average speed calculated is not affected by the time of interruption. Some runners also run in place while stopped. A third stride type for running in place, in addition to walking and running, may be added to the stride analysis. Strides recognized as being running in place would be given a stride length of zero.

It can also be appreciated that the stride length data calculated can be communicated to another device either through a removable wire connection or via a radio-frequency or optical means of data transmission. For example, the stride length data can be transmitted to a display device worn on the wrist of the user like a wristwatch. This makes the distance and speed information more readily accessible to the user while walking and running. If optical means of data transmission such as an infrared transmitter and receiver is used, then the display device is worn on the wrist opposite the foot to which the pedometer is attached. This arrangement gives an unimpeded line of sight for data transmission for a sufficiently long interval during each stride.

Thus the scope of the invention should be determined by the appended claims and their legal equivalents, rather than by the examples given.

We claim:

1. A device for measuring the length of the stride of a human user while walking or running comprising:
   (a) an accelerometer for providing an acceleration signal indicative of the acceleration of the foot of said user, said accelerometer being attached to said foot of said user;
   (b) processor memory for storing data related to the walking and running activity of said user, including a plurality of acceleration values of said foot of said user, time interval data indicating the length of a measurement interval, predetermined data indicative of the typical acceleration values of the human foot while walking and running, and data indicative of the stride of said user, said processor memory comprising in part non-volatile memory for storing data used to calculate the stride length for said user;
   (c) a data processor coupled to said accelerometer, and said processor memory, said data processor being configured to:
      (1) sample a plurality of values of said acceleration signal at redefined time intervals and store said time-varying sequence of acceleration values indicating the variation in the acceleration signal over time in said processor memory;
      (2) compare said time-varying sequence of acceleration values to predetermined data indicative of typical accelerations of the human foot caused by walking and running, determine a correlation between said sequence of acceleration values and strides of said user's foot, and determine whether said user is walking or running;
      (3) determine a plurality of stride profile data values from said time-varying sequence of acceleration values for each stride of said user's foot said stride profile data values indicative of the length of said user's stride;
      (4) determine the length of each said stride from said stride profile data values;
      (5) and determine the total distance traveled by adding the lengths of the strides taken by said user;

(d) an output means to communicate information to said user, whereby said output means will display the total distance traveled by said user, and whereby a walker or runner knows the total distance traveled while walking and running.

2. The device for measuring the length of the stride of a human user while walking or running of claim 1, wherein said output display is a liquid crystal display (LCD).

3. The device for measuring the length of the stride of a human user while walking or running of claim 1, comprising an output device, said output device being coupled to the data processor by means of optical data transmission, whereby the distance traveled by the human user is displayed on said output device.

4. The device for measuring the length of the stride of a human user while walking or running of claim 1, further including a timer for measuring intervals of time, whereby the device determines the traveling speed of said user.

5. The device for measuring the length of the stride of a human user while walking or running of claim 1, further including a means for inputting information coupled to the data processor whereby said user can select one of a plurality of modes of operation of said data processor.

6. The device for measuring the length of the stride of a human user while walking or running of claim 5, wherein said input means is a pushbutton switch.

7. A method of determining a length of each stride taken by a user while walking and running, the method comprising the following steps:

(a) measuring at predefined time intervals a plurality of acceleration values corresponding to the variable acceleration of one foot of said user over time while walking and running;

(b) providing a memory which is able to store said time-varying sequence of acceleration values;

(c) comparing said time-varying sequence of acceleration values to predetermined data indicative of typical accelerations of the human foot caused by walking and running;

(d) correlating said time-varying sequence of acceleration values and the strides of said user's foot, and determining whether said user is walking or running;

(e) determining a plurality of stride profile data values from said time-varying sequence of acceleration values for each stride of said user's foot, said stride profile data values indicative of the length of said user's stride;

(f) determining the length of each said stride from said stride profile data values.

8. The method for determining the length of each stride taken by a human user while walking and running of claim 7, wherein the accelerations of the user's foot is provided by an accelerometer attached to said user's foot.

9. The method for determining the length of each stride taken by a human user while walking and running of claim 7, wherein the length of each walking stride is determined from the set of stride profile data values by means of a linear formula using a set of predetermined coefficients.

10. The method for determining the length of each stride taken by a human user while walking and running of claim 9, wherein the set of coefficients of the linear formula are determined by a calibration procedure comprising the following steps:

(a) collecting walking stride profile data for the strides of the user while walking a predetermined distance at a constant speed, and determining the stride length for each stride profile collected by dividing said predetermined distance by the number of steps taken;

(b) collecting walking stride profile data and associated stride length data for a plurality of different walking speeds;

(c) determining a set of coefficients used to determine the stride length for walking strides by means of a method of multiple linear regression.

11. The method for determining the length of each stride taken by a human user while walking and running of claim 7, wherein the length of each running stride is determined from the set of stride profile data values by means of a linear formula using a set of predetermined coefficients.

12. The method for determining the length of each stride taken by a human user while walking and running of claim 11, wherein the set of coefficients of the linear formula are determined by a calibration procedure comprising the following steps:

(a) collecting running stride profile data for the strides of the user while running a predetermined distance at a constant speed, and determining the stride length for each stride profile collected by dividing said predetermined distance by the number of steps taken;

(b) collecting running stride profile data and associated stride length for a plurality of different running speeds;

(c) determining the set of coefficients used to determine the stride length for running strides by means of the method of multiple linear regression.

* * * * *